United States Patent [19]
Matthews et al.

[11] Patent Number: 5,830,770
[45] Date of Patent: Nov. 3, 1998

[54] HAPTEN-PROTEIN CONJUGATES FOR USE IN DETECTION OF ORGANOPHOSPHORUS COMPOUNDS

[75] Inventors: Wendy Alison Matthews; John Nicholas Banks; Mohamed Qasim Chaudhry, all of Slough, United Kingdom

[73] Assignee: The Minister of Agriculture Fisheries and Food in Her Britannic Majesty's Government of the U.K. of Gt. Britain & N. Ireland, United Kingdom

[21] Appl. No.: 557,003

[22] PCT Filed: May 18, 1994

[86] PCT No.: PCT/GB94/01060

§ 371 Date: Apr. 25, 1996

§ 102(e) Date: Apr. 25, 1996

[87] PCT Pub. No.: WO94/27149

PCT Pub. Date: Nov. 24, 1994

[30] Foreign Application Priority Data

May 18, 1993 [GB] United Kingdom .................. 9310238

[51] Int. Cl.$^6$ ........................ G01N 33/531; G01N 33/53; C07K 16/00
[52] U.S. Cl. ........................ 436/543; 435/7.92; 435/7.93; 436/547; 436/548; 530/388.9
[58] Field of Search .................... 435/7.92, 7.93; 436/547, 548, 543; 530/388.9

[56] References Cited

U.S. PATENT DOCUMENTS

| | | | |
|---|---|---|---|
| 5,283,180 | 2/1994 | Zomer et al. | 435/8 |
| 5,413,915 | 5/1995 | Case et al. | 435/25 |
| 5,589,624 | 12/1996 | Ulbrich et al. | 800/205 |

*Primary Examiner*—James C. Housel
*Assistant Examiner*—Rodney P. Swartz
*Attorney, Agent, or Firm*—Nixon & Vanderhye

[57] ABSTRACT

Novel generic antibodies are provided that are specific to groups of organophosphates, particularly to a class of organophosphate pesticides in common usage. Further provided are compounds and methods for raising these antibodies, test kits containing them and methods for their use. The antibodies targeted at low molecular weight (i.e. below MW 1000) organophosphorous pesticides methacrifos, pirimphos methyl, etrimfos, fenitrothion, chlopyrifos methyl, dichlorovos and malathion. Preferred conjugates of the invention are of the formula $(RO)_2-P(S)-Z-[Y]$-Protein wherein R is lower alkyl and Z is as O, S or —NH—, Y is a spacer group and "Protein" indicates a protein suitable for use in hapten protein conjugates for the purpose of raising antibodies and antisera. Typical and preferred proteins are bovine serum albumin, ovalbumin from chicken egg, keyhole limpet hemocyananin and mixtures of these.

3 Claims, 2 Drawing Sheets

O-2- Diethylamino-6-methylpyrimidin-4-yl O,O-dimethylphosphorothionate
Pirimiphos-methyl O-2- Diethylamino-6-methylpyrimidin-4-yl O,O-diethylphosphorothionate
Pirimiphos-ethyl O,O-dimethyl O-3,5,6-trichloro-2-pyridylphosphorothionate
Chlorpyrifos-methyl O-6-ethoxy-2-ethlypyrmindin-4-ylO,O-dimethylphosphorothionate
Etrimfos

O,O-Dimethyl O-4nitro-m-tolylphosphorothionate
Fenitrothion

2,2-Dichlorovinyl dimethylphosphate
Dichlorvos

Diethyl (dimethoxythiophosphorylthio)succinate
Malathion

Methyl (E)-3-(dimethoxyphosphinothioyloxy)-2-methylacrylate
Methacrifos

HAPTEN-PROTEIN CONJUGATES FOR USE IN DETECTION OF ORGANOPHOSPHORUS COMPOUNDS

The present invention relates to novel generic antibodies that are specific to groups of organophosphates, particularly to a class of organophosphate pesticides in common usage. Further provided are hapten compounds and methods for using them in raising these antibodies, test kits containing them and methods for their use.

A number of immunoassays are available for the detection of various biologically important compounds. Such compounds include the important organophosphate (OP) class of pesticides (see eg. WO 91/00294). These immunoassays are relatively sensitive, but are directed against individual OP molecules and thus several separate assays are required to effectively screen a material for OP presence.

A group of these organophosphate pesticides that is commonly used for foodstuff, eg. grain, protection comprises the compounds methacrifos, pirimphos methyl, fenitrothion, etrimfos, propetamphos, chlopyrifos methyl and dichlorvos, and screening a material for the presence of any of these potentially toxic compounds conventionally requires use of seven separate agents. While these compounds share some chemical features with each other, including that of the OP group itself, other commonly used pesticides are distinguished by variant OP groups. In malathion for example a $(CH_3O)_2P(S)—S—$ group is present as compared to the $(CH_3O)_2P(S)—O—$ group of the compounds referred to above.

The present inventors have now provided a novel strategy for raising antibodies such that they are specifically directed to bind with two or more of these specified pesticidal organophosphorous compounds and further provide methods for using these and kits containing them, such that materials can be screened for presence of a member of a selected group with a single antibody reagent. Still further they have provided organic haptens and their conjugates which may be used specifically to raise these antibodies, or antisera containing them, as either monoclonal or polyclonal antibodies. Particularly provided are antibodies capable of specific binding with two or more, more preferably three or more, and most preferably all of the compounds methacrifos, fenitrothion, etrimfos, propetamphos, dichlorvos and optionally one or more of malathion, dimethoate, chlorfenvinphos, chlopyrifos methyl, tetrachlorvinphos and pirimiphos-methyl, wherein the relative binding affinity with each of these bound compounds is such that a single strength antibody reagent can be used to bind them. Preferably the OPs bound are capable of displacing percentages of bound hapten from the antibody at a concentration of 100 µg/ml within a factor of 20, more preferably of 5, and more preferably 2 of each other. Also provided are haptens and hapten-protein conjugates which evoke production of such antibodies when adminstered to animals.

The concept that one generic antibody or antisera might be raised to be capable of detecting a number of organophosphates has been considered on one occasion previously by Suedi and Heesham Kiel: (1988) Milchwirt Forsch 40 179–202, but this involved use of a number of model pesticide molecules to provide a number of protein conjugates. Furthermore the antibody reagents obtained were not capable of use in reliable screening.

In a first aspect of the present invention there is provided a hapten protein conjugate capable of stimulating production of antibodies which have specific binding affinity for compounds including the chemical moiety I:

$$(RO)_2P(S)—A— \quad\quad (I)$$

wherein R is lower alkyl, particularly $C_{1-4}$ alkyl, and A is O or S; characterised in that the antibody binds two or more, preferably three or more, and most preferably all of the compounds methacrifos, fenitrothion, propetamphos, dichlorvos, dimethoate, malathion, chlorfenvinphos and etrimfos; preferably also binding to chlopyrifos methyl, tetrachlorvinphos and pirimiphos-methyl.

Most preferably the conjugates evoke production of antibodies targeted at moiety (I) where R is methyl, and preferably where A is O, wherein cross-reactivity with other compounds relative to those having this moiety is low enough to enable ready identification of the targeted compounds in a mixture by binding with a known antibody concentration.

Preferred hapten protein conjugates of the invention are of formula (II):

$$(RO)_2—P(S)—Z—[Y]\text{-Protein} \quad\quad (II)$$

wherein R is as defined for moiety (I) and Z is O, S or —NH—, Y is a spacer group and 'Protein' indicates a protein suitable for use in hapten-protein conjugates for the purpose of raising antibodies and antisera. Typical and preferred proteins are bovine serum albumin, ovalbumin from chicken egg, keyhole limpet hemocyanin and mixtures of these. Preferably linkage to protein is by one of its amino groups.

Preferred spacer groups are format —$(CH_2)_n$—B— wherein n is such that the carbon chain length is 4 to 6 and B is CO or O(CO), or the spacer is a pyridine or pyrimidine ring with a CO or O(CO) group. Optionally the spacer may have side chains, eg. as in compounds such as β-alanine as disclosed by WO 9100294, but the most preferred conjugates of the invention have a straight carbon chain of 4–6 eg. a 1,4-butanediol spacer whereby Z is O and B is —O(CO)— provided by way of carbodiimide activation of the —OH end group. Examples of suitable haptens are listed as follows:

$(CH_3O)_2—P(S)—O—(CH_2)_4—O—CO—NH\text{-Protein}$ (butandiol spacer)
$(CH_3O)_2—P(S)—O—(CH_2)_4—CO—NH\text{-Protein}$ (butandiol spacer)
$(CH_3O)_2—P(S)—O—CH_2—CH_2—O—CO—NH\text{-Protein}$ (3 carbon spacer)
$(CH_3O)_2—P(S)—O—CH_2—CH_2—CO—NH\text{-Protein}$ (3 carbon spacer)
$(CH_3O)_2—P(S)—O—CH_2—O—CO—NH\text{-Protein}$ (2 carbon spacer)
$(CH_3O)_2—P(S)—O—CH_2—CO—NH\text{-Protein}$ (2 carbon spacer)
$(CH_3O)_2—P(S)—S—CH_2—CH_2—O—CO—NH\text{-Protein}$ (SH-linked spacer)
$(CH_3O)_2—P(S)—S—CH_2—CH_2—CO—NH\text{-Protein}$ (SH-linked spacer)
$(CH_3O)_2—P(S)—O\text{-pyridine-}O—CO—NH\text{-Protein}$ (pyridine spacer)
$(CH_3O)_2—P(S)—O\text{-pyridine-}CO—NH\text{-Protein}$ (pyridine spacer)
$(CH_3O)_2—P(S)—O\text{-pyrimidine-}O—C—NH\text{-Protein}$ (pryrimidine spacer)
$(CH_3O)_2—P(S)—O\text{-pyrimidine-}CO—NH\text{-Protein}$ (pryrimidine spacer)

In a second aspect of the invention there are provided hapten compounds of formula (III) for use in preparing compounds (II):

$$(RO)_2—P(S)—Z—(Y)—B—(D) \quad\quad (III)$$

wherein R, Z, B and Y are as described above and D is H or an activator group. Typical activator groups are those such as imidazole residues of the type left by activation with carbodiimides, but halogen atoms may also used where B is CO, such as to form an acid halide, capable of activating reaction between the compound and protein amino groups. Particularly provided are hapten compounds of formula (IV):

(RO)₂P(S)—O—(Y)—B—(D)                            (IV)

wherein Y is a spacer of four carbon length, with or without side chains, preferably being a —(CH₂)₄— moiety. Most preferably B is O—CO— and D is an imidazole residue. Where D is H the compound is an unactivated hapten, otherwise the compound is in the activated form.

Further provided by the present invention is a method for synthesis of the haptens and conjugates of formula (II), (III) and (IV) wherein a dialkyl halothiophosphate is reacted with a spacer group precursor to produce the hapten. The resultant hapten is then activated with an activator moiety to provide the activated product and that is conjugated with the protein to provide a protein conjugate of formula (II) in the usual manner.

The dialkyl halothiophosphate/spacer group reaction is conveniently carried out in organic solvent phase with a base, eg. pyridine, and at low temperature, eg between -5° and 10° C., preferably 0° and 5° C. Acetone solvent is conveniently used. The reaction mixture is preferably shaken or stirred with the spacer group being dissolved in the solvent/base mixture and the dialkyl halothiophosphate being added slowly to this before reflux, that preferably being at about 60° C. for a period of several, but most preferably about two, hours. The activation of the hapten is conveniently carried out using a carbodiimide, eg. carbonyl diimidazole, in the known manner and this activated hapten is then conjugated with the selected protein.

The antibodies and antisera produced using these conjugates of the invention can be raised by any of the methods conventionally used in the art using any of the conventional animal donors. Furthermore the antibodies so raised may be polyclonal or monoclonal; the latter being derivable by hybridoma technology as will be well understood by those skilled in the art.

BRIEF DESCRIPTION OF THE DRAWINGS

For OP formulae see FIGS. 1A, 1B, 1C, 2A, 2B, 2C, 2D and 2E. The present invention further provides test kits comprising the antibodies or antisera of the invention together with other items specific for the determination of the presence of the target organophosphates in a material. Such items may include calibration reagents containing a known amount of target OP compound, or may take the form of antibodies immobilised on a substrate, eg. on microtitre well plates or the like, whereby absorbance values may be readily obtained at suitable wavelength, eg. 450 nm, to determine antibody titre, or other reagents such as specific buffers, blocking agents or colour developers. Typical kit formats are as discussed in WO 9100294.

The production of antibodies and the antisera containing them, and their use in assays, is carried out using known methods and is exemplified in the Examples. The haptens, conjugates, antibodies, antisera and methods of the present invention will now be described by way of example only by reference to the following non-limiting Examples.

EXAMPLE 1

Figure 1A:
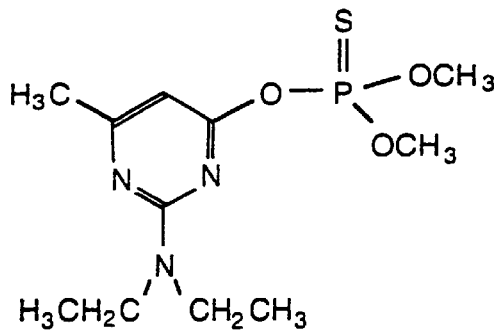
Figure 1B:
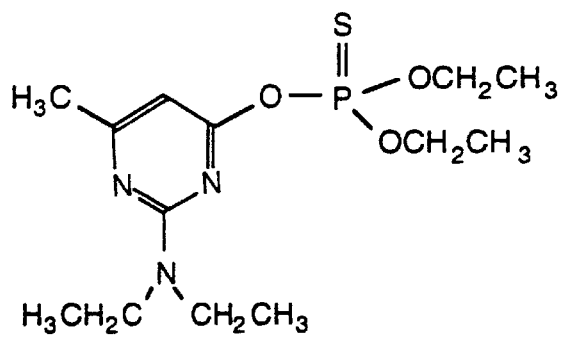
Figure 1C:
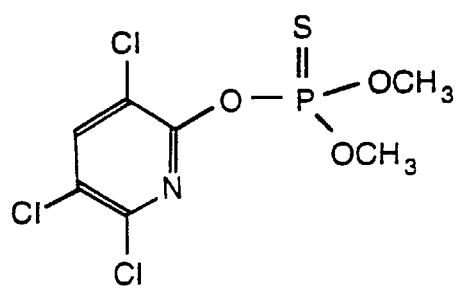
Figure 2A:
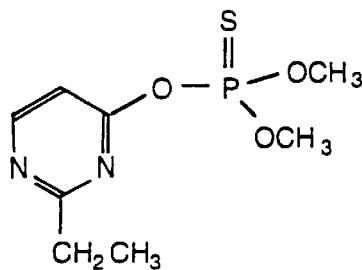
Figure 2B:
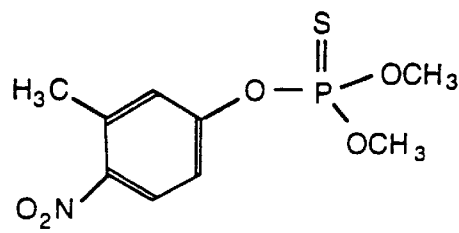
Figure 2C:
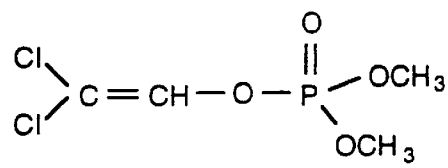
Figure 2D:
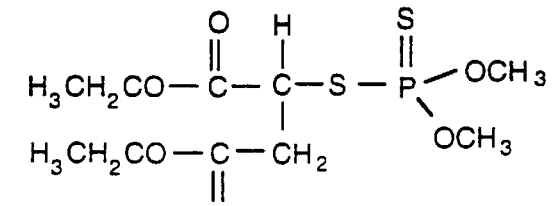
Figure 2E:
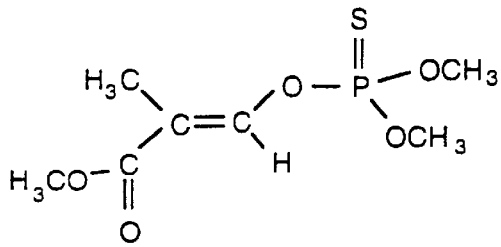

Synthesis of Generic Organophosphate Antibody Generating Conjugate Hapten Intermediate of Formula (III) and (IV)

10 mmoles of pyridine (0.79 g) were dissolved in 5 ml acetone and the solution kept on ice. To this was added 10 mmoles of 1,4 butanediol (0.90 g) and with constant shaking of the chilled mixture using a magnetic stirrer 10 mmoles of dimethylchlorothiophosphate $(CH_3O)_2$—P(S)Cl (1.61 g) was slowly added. The reactants were refluxed at 60° C. for 2 hours and then left overnight at room temperature (Reaction A).

The final product was purified by extracting the mixture of reactants with 3×25 ml of diethylether, washing that with 3×10 ml of $H_2O$ and then evaporating it to a final volume of about 2 to 3 ml. Formation of $(CH_3O)_2P(S)$—O—$(CH_2)_4$—OH (mol wt. 214) was indicated on TLC (Rf=0.1 in chloroform:acetone 70:30) and confirmed on GC/MS.

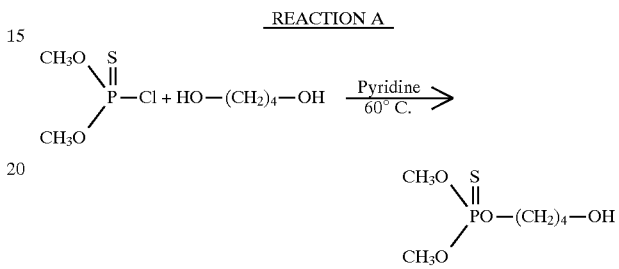

EXAMPLE 2

Activation of Hapten

Example 1 was treated with 10 mmoles (1.62 g) of carbonyl diimidazole thus providing activated hapten solution. (NB. Where B is a carboxyl group thionyl halide may be used to produce the corresponding acid halide in the known manner).

EXAMPLE 3

Formation of Protein Conjugates 3 mmoles of activated hapten from Example 2, in the form of 1 ml of the ethereal solution, was added very slowly—one drop every five minutes—to each of three protein solutions whilst constantly stirring using a magnetic stirrer; these containing 30 μmoles of BSA or Ovalbumin, or 3 nmoles of Keyhole Limpet hemocyanin respectively in 10 ml phosphate buffer saline pH 7.4. Reactants were stirred slowly for 2 hours, left overnight at room temperature and then at 4° C. for 72 hours (see Reaction B). The conjugate solutions were analysed for the concentration of protein using the Coomassie blue method of Bradford: Analytical Biochem. (1976) 72:248–254. The ratio of the conjugation was found by the free amino group method of Habeeb as in Analytical Biochem (1966) 14:328–336 as an OP:BSA of 10 and an OP:Ovalbumin of 4.

Purification of conjugate was effected by application to Sephadex (PD 10) columns, with dialysis of insoluble or sparingly soluble conjugates against distilled water being carried out as a preparatory step prior to application.

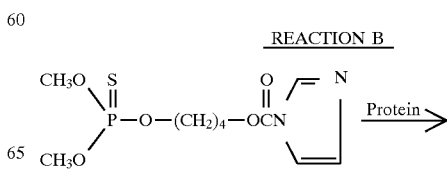

-continued
REACTION B

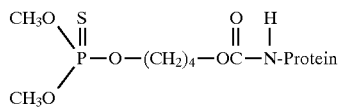

EXAMPLE 4

Production of Polyclonal Antibodies to Generic Conjugate

Simone Noir half lop rabbits were housed individually and allowed 3 weeks to settle in before pre-immunisation blood samples were taken and the immunisation schedule started. Hapten-Bovine serum albumin (BSA) conjugates were first mixed with equal volumes of Freund's adjuvant so that the final concentration was about 1 mg/ml of protein.

After testing to show the absence of native antibodies reactive with the conjugates, each rabbit was given subcutaneous injections of 1 ml of the BSA generic conjugate of Example 3 spread over 4 sites (0.25 ml per site) in complete adjuvant. Subsequent injections were given at 4, 8 and 12 weeks in incomplete adjuvant. When the antibody titre started to fall the rabbits were boosted with a further 1 ml of conjugate in Freund's incomplete adjuvant spread over 4 sites. In the tables below rabbits R19,20,21 were immunised with this generic conjugate, ratio OP hapten:protein of 10:1, of the invention.

Blood was taken from the marginal ear vein prior to immunisation for antibody checks and at 4 and 14 weeks after injection in order that antisera stocks could be built up. Antisera were prepared by allowing blood to clot overnight at 4° C. and then centrifuging it to provide clear fluid. Antibodies could be isolated from this as required by use of ion exchange or affinity column chromatography with immobilised target organophosphate groups in the conventional manner.

EXAMPLE 5

Indirect:Antibody Capture Enzyme Linked Immunosorbent Assay (ELISA) Demonstrating Affinity of Antisera for Moiety of Formula (I)

An ELISA was used to screen the antisera for polyclonal antibodies to the generic hapten/conjugate of the invention using the following protocol. Microtitre plates (Costar) were coated with the appropriate hapten conjugate with ovalbumin by diluting that in 0.05M sodium hydrogen carbonate/sodium carbonate buffer (pH 9.6) to give an optimum protein concentration of 1 µg/ml previously determined by chequerboard titration; protein found by Bradford assay. 100 µl was added to each microtitre plate well and the plates placed in a moist chamber overnight, washed 3 times with 0.15 phosphate buffered saline pH7.2 with 0.05% Tween 20[RTM]: PBST), and blotted dry. Blocking was carried out by adding 250 µl per well of 5% skimmed milk for 1 hour at 25° C.

After two further washings the coated microplates were stored at −20° C. until required, whereon they were washed once with PBST. Antisera were diluted (1/1000 for general screening or doubling dilutions up to 1/512,000 for titration assays) in PSBT, applied to microtitre wells in triplicate in 50 µl amounts and incubated in a moist chamber at 25° C. for 1 hour (appropriate positive and negative controls were included—PBST, negative rabbit serum and positive serum when it had been produced). Wells were then washed 3 times in PBST and 200 µl of a 1:1500 dilution of swine anti-rabbit immunoglobulin conjugated to horseradish peroxidase (DAKO) was added to each well. Plates were incubated once more for 1 hour at 25° C. then washed 3 times with PBST.

Tetramethylbenzidine (TMB) enzyme substrate solution was prepared by adding 400 µl of 6.0 g/l TMB in DMSO to 24.5 ml of 0.1M sodium acetate buffer pH5.5 with 100 µl of 1% $H_2O_2$ and 100 µl added to the wells. The microplates were incubated for 15 minutes in the dark at 25° C. before the reaction was stopped by adding 50 µl of 2.5M $H_2SO_4$ and the absorbance read at 450 nm against air. Results: are given below with those of Example 6.

EXAMPLE 6

Competitive/Inhibition Assay

This assay was carried out in the same manner as that of Example 5 with the following modifications. After plate coating the various dilutions of antisera were incubated with various concentrations of analyte solution for 1 to 2 hours at 25° C. or overnight at 4° C. Antiserum dilutions tested were 1/1000, 1/2000, 1/5000 and 1/10000 and the concentrations of the analyte ranged from 200 to 0.001 µg/ml. Coating of generic hapten-ovalbumin was at 1 µg/ml and later other coating strengths were tested ranging from 400 to 12.5 ng/ml. Note: cross reactivity in all cases was checked by carrying out an indirect ELISA where plates were coated with the blocking agents or BSA or ovalbumin at 1 µg/ml. Skimmed milk, foetal calf serum (both 5%), caesin (0.3%) or fish skin gelatin (0.5%) were selected as the blocking agent in this regard. Use of competitive assay is preferred for determining cross-reactivity.

Results: Sera collected at 4 and 16 weeks showed reactivity with the conjugate, and chequerboard titrations at 16 weeks (see Table 1 and 2) showed all three rabbit's sera to be strongly reactive. Optimum coating of wells with the conjugate proved to be achieved with about 1 µg/ml, giving high absorbance with antisera and low absorbance with negatives. It should be noted that cross-reaction with spacer moiety or protein alone may occur; skimmed milk coated, gelatin blocked plates were shown to obviate this sufficiently for successful ELISA.

Table 3 shows the results of the competitive/inhibition ELISA indicating that the coating levels should be less than 1 µg/ml for optimal sensitivity: eg. 400 to 0.012 µg/ml conjugate for 200 to 0.001 µg/ml analyte detection.

TABLE 1

Chequerboard absorbance with values for 16 week generic BSA conjugate antisera (1/1000) with coating concentrations of 20 to 0.16 µg/ml OP-Ova

| Coating Conc. | Rabbit 19 | Rabbit 20 | Rabbit 21 | Negative |
|---|---|---|---|---|
| 20.0 | 2.22 | 2.30 | 2.22 | 0.17 |
| 10.0 | 2.15 | 2.20 | 2.21 | 0.16 |
| 5.0 | 2.05 | 2.21 | 2.18 | 0.14 |
| 1.25 | 1.87 | 2.11 | 2.06 | 0.13 |
| 0.63 | 1.51 | 2.07 | 1.99 | 0.14 |
| 0.32 | 1.36 | 1.94 | 1.86 | 0.18 |
| 0.16 | 0.92 | 1.75 | 1.41 | 0.21 |

TABLE 2

Absorbance values for 16 week generic BSA conjugate antisera screen and dilution when negative (absorbance <0.2) plate coated at 1 μg/ml with OP-Ova at 1 μg/ml.

| Rabbit No. | Absorbance (serum 1/1000) | Dilution when negative (<0.2) |
|---|---|---|
| 19 | 2.44 | 1/512000 |
| 20 | 2.56 | 1/512000 |
| 21 | 2.56 | 1/512000 |

TABLE 3

Competitive/inhibition assay for antisera from rabbits 19, 20, 21 pre-incubated with various concentrations of unconjugated organophosphate (OP) for 1 hour at 25° C.: 1 μg/ml OP-Ova

| Conc. of OP μg/ml as preincubated with antisera | Rabbit 19 | Rabbit 20 | Rabbit 21 |
|---|---|---|---|
| 50.0 | 1.34 | 1.19 | 1.24 |
| 12.5 | 1.36 | 1.31 | 1.02 |
| 3.1 | 1.50 | 1.54 | 1.34 |
| 0.4 | 1.66 | 1.81 | 1.45 |
| 0.1 | 1.73 | 1.95 | 1.42 |
| 0.01 | 1.83 | 1.95 | 1.52 |
| Without OP | 2.30 | 2.39 | — |
| -ve serum | 0.13 | 0.13 | 0.15 |

TABLE 4

Competitive/inhibition assay for antisera: preincubated with OP for 2 hours at 25° C. Plate coated with 400 μg/ml OP-Ova.

| OP conc as preinc' with antisera | Dilution of Rabbit 20 antisera | |
|---|---|---|
| | 1/1000 | 1/2000 |
| 200.0 | 0.89 | 0.69 |
| 100.0 | 0.82 | 0.67 |
| 20.0 | 0.87 | 0.67 |
| 10.0 | 0.94 | 0.74 |
| 1.0 | 1.24 | 0.87 |
| 0.1 | 1.48 | 1.04 |
| 0.01 | 1.58 | 1.11 |
| 0.001 | 1.38 | 1.10 |
| Without OP | 2.00 | 1.69 |

EXAMPLE 7

Modified Competitive Inhibition Assay

Assay was carried out in the same manner as Example 5 with the following modifications. Antisera was diluted 1:2000 with 1% BSA in PBST and 100 μl was incubated for 2 hours at 25° C. with 100 μl of each concentration of the unconjugated OP—in this case the generic part—in a microtitration plate. Concentrations of OP ranged from 200 to 0.001 μg ml$^{-1}$.

Cross reactivity of antisera from rabbits 19, 20 and 21 by inhibition ELISA with the various organophosphorus pesticides is shown in Table 5 in which concentration (μg ml$^{-1}$) for 50% inhibition to occur is given together with the diluent in which this is achieved—PBST or % methanol in PBST for figures.

TABLE 5

| Inhibitor | Rabbit 19 | Rabbit 20 | Rabbit 21 |
|---|---|---|---|
| Hapten + spacer | +++ | +++ (3.0 PBST) | +++ |
| Hapten no spacer | ++ | poor | ++ |
| Spacer | – (none) | – (none) | – (none) |
| Fenitrothion | + | +++ (4.8 10%) | + |
| Methacrifos | + | +++ (8.2 PSBT) | + |
| Propetamphos | + | +++ (36.2 10%) | ++ |
| Dichlorvos | ++ | ++ (91.1 PSBT) | + |
| Dimethanoate | – (none) | ++ (>150 10%) | + |
| Malathion | – (none) | + | – (none) |
| Chlorfenvinphos | – (none) | + | + |
| Etrimfos | – (none) | + | poor |
| Chlorpyrifosmethyl | poor | poor | poor |
| Tetrachlorvinphos | – (none) | poor | poor |
| Pirimiphos-methyl | – (none) | poor | – (none) |
| Glyphospate | – (none) | – (none) | – (none) |

+++ strong
++ medium
+ weak reaction
poor—slight

The relative affinities of the various organophosphates for the generic conjugate antibodies as shown by the results from Example 7 are provided below as derived by subtracting the amount of inhibition of binding at a concentration of 0.1 μg/ml organophosphate from that obtained with 100 μg/ml organophosphate; results are presented as % of the inhibition obtained with hapten including spacer as the inhibitor.

TABLE 6

Relative inhibition of binding of generic antibodies to hapten conjugate as % of hapten + spacer inhibition

| Organophosphate | Percentage inhibition |
|---|---|
| Hapten-spacer | 100.0 |
| Fenitrothion | 90.1 |
| Methacrifos | 89.1 |
| Propetamphos | 75.9 |
| Dichlorvos | 60.0 |
| Dimethoate | 41.4 |
| Malathion | 38.6 |
| Chlorfenvinphos | 33.4 |
| Etrimfos | 30.8 |
| Chlorpyrifos-methyl | 29.2 |
| Tetrachlorvinphos | 27.2 |
| Pirimiphos-methyl | 21.1 |

We claim:

1. A hapten-protein conjugate having the formula:
   $(CH_3O)_2$—P(S)—O—$(CH_2)_4$—O—CO—NH-Protein, or
   $(CH_3O)_2$—P(S)—O—$(CH_2)_4$—CO—NH-Protein
   wherein Protein indicates a protein suitable for use in said hapten-protein conjugate for the purpose of raising antibodies, antisera or use in immunoassays.

2. A conjugate as claimed in claim 1 wherein the protein is selected from the group consisting of bovine serum albumin, ovalbumin from chicken egg and keyhold limpet hemocyanin.

3. A method for synthesis of said hapten protein conjugate of claim 1 comprising (a) reacting a dialkyl halothiophosphate with a spacer group to produce said hapten, (b) activating the resultant hapten with an activator moiety to provide an activated product, and (c) reacting the product of step (b) with the protein.

* * * * *